United States Patent [19]

Boar et al.

[11] Patent Number: 5,712,299
[45] Date of Patent: Jan. 27, 1998

[54] (1-PHENYL-1-HETEROCYCLYL)METHANOL AND (1-PHENYL-1-HETEROCYCLYL METHYLAMINE DERIVATIVES

[75] Inventors: Robin Bernad Boar, Herts; Alan John Cross, Surrey; Duncan Alastair Gray, Powys; Richard Alfred Green, Oxon, all of Great Britain

[73] Assignee: Astra Aktiebolag, Sodertalje, Sweden

[21] Appl. No.: 379,469

[22] PCT Filed: Jul. 5, 1994

[86] PCT No.: PCT/SE94/00665

§ 371 Date: Jan. 30, 1995

§ 102(e) Date: Jan. 30, 1995

[87] PCT Pub. No.: WO95/01968

PCT Pub. Date: Jan. 19, 1995

[30] Foreign Application Priority Data

Jul. 3, 1993 [SE] Sweden ................ 9302324

[51] Int. Cl.$^6$ .............. C07D 203/30; C07D 277/30; A61K 31/42; A61K 31/425
[52] U.S. Cl. .............. 514/365; 514/359; 514/374; 548/100; 548/203; 548/235
[58] Field of Search ............. 548/100, 203, 548/235; 514/354, 365, 374

[56] References Cited

PUBLICATIONS

Hodges, J. Org. Chem. 56(1) 449 (1991).
Dondeni, J. Org. Chem 53(8) 1748 (1988).
Ashton, J. Med. Chem. 27(10) 1245 (1989).
Craig J. Org. Chem 22 559 (1957).

*Primary Examiner*—Robert Gerstl
*Attorney, Agent, or Firm*—White & Case

[57] ABSTRACT

The present invention relates to novel heterocyclic compounds having the general formula (1)

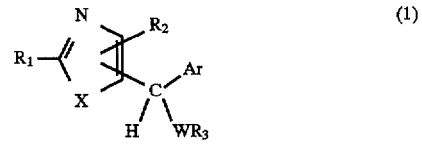

wherein:

X is O, S or Se;

$R_1$ is H, lower alkyl, lower alkoxy-lower alkyl, aryl-lower alkyl or $CF_3$;

$R_2$ is H, lower alkyl, lower alkoxy-lower alkyl, aryl-lower alkyl or $CF_3$;

W is O, S, NH or N-lower alkyl;

$R_3$ is H, lower alkyl or lower acyl;

Ar is phenyl, furyl, thienyl, naphthyl, pyridyl or pyrrolyl, optionally substituted by $R_6$;

$R_6$ is one or more groups selected from lower alkyl, lower acyl, halogen, lower alkoxy, $CF_3$, OH, $NO_2$ or $NR_4R_5$, wherein $R_4$ and $R_5$ independently are H, lower alkyl or lower acyl;

geometrical and optical isomers and racemates thereof where such isomers exist, as well as pharmaceutically acceptable acid addition salts thereof and solvates thereof having therapeutic activity, processes and intermediates for their preparation, pharmaceutical formulations containing said compounds and the medicinal use of said compounds.

6 Claims, No Drawings

(1-PHENYL-1-HETEROCYCLYL)METHANOL AND (1-PHENYL-1-HETEROCYCLYL METHYLAMINE DERIVATIVES

This application is a 371 of PCT/SE94/00665 filed Jul. 5, 1994.

1. Field of the Invention

The present invention relates to novel heterocyclic compounds having therapeutic activity, processes and intermediates for their preparation, pharmaceutical formulations containing said compounds and the medicinal use of said compounds.

2. Background of the Invention

There exists a large group of acute and chronic neuropsychiatric disorders for which safe and clinically effective treatments are not currently available. This diverse group of disorders encompasses a broad spectrum of initial events which are characterised by the initiation of progressive processes that sooner or later lead to neuronal cell death and dysfunction. Stroke, cerebral ischaemia, trauma or a neurodegenerative disease such as Alzheimer's disease or Parkinson's disease are all commonly occurring conditions that are associated with neurodegeneration of the brain and/or spinal cord.

The ongoing search for potential treatments of neurodegenerative disorders has involved investigation of excitatory amino acid antagonists, inhibitors of lipid peroxidation, calcium channel antagonists, inhibitors of specific pathways of the arachidonic acid cascade, kappa opioid agonists, adenosine agonists, PAF antagonists and diverse other agents. At the present time there is no consensus of the relative importance of the role played by compounds belonging to any of these general classes.

Anticonvulsant agents are widely used, particularly for the treatment of various types of epilepsy. In general, the mechanism of action of such agents is poorly understood and there remains a genuine need for the development of new safe and effective anticonvulsants.

In a paper (J. Org. Chem., 1957, 22, 559–561) on the synthesis of heterocyclic aminoethers related to the antihistamine diphenhydramine, the compounds 1-(4-methyl-5-thiazolyl)-1-phenylmethanol and 1-(2,4-dimethyl-5-oxazolyl)-1-phenylmethanol are described as intermediates.

In J. Org. Chem., 1988, 53, 1748–1761, 1-(5-thiazolyl)-1-phenylmethanol is disclosed.

In J. Org. Chem., 1991, 56, 449–452, 1-(4-oxazolyl)-1-phenylmethanol is described.

In J. Med. Chem., 1984, 27, 1245–1253, 1-(2,4-dimethyl-5-thiazolyl)-1-(2-cholrophenyl) methanol is disclosed as an intermediate in the synthesis of certain heterocyclic analogues of chlorcyclizine with hypolipidemic activity.

No pharmacological activity is ascribed to any of the above confounds. These five compounds are deleted from the scope of the present invention by a disclaimer in claim 1.

In patent application EP 351 194, the compounds;

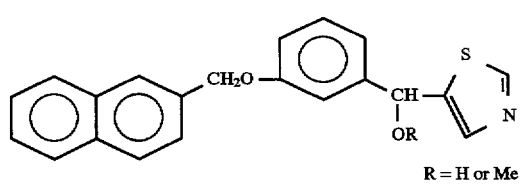

R = H or Me are disclosed. The substituent 2-naphthylmethyloxy is not included within the scope of $R_6$ of the present invention.

The present invention

A primary objective of the present invention is to provide structurally novel heterocyclic compounds which by virtue of their pharmacological profile are expected to be of value as neuroprotective agents, as anticonvulsant agents and/or as sedative-hypnotics.

Neuroprotective agents are useful in the treatment of acute and chronic neuropsychiatric disorders characterised by progressive processes that sooner or later lead to neuronal cell death and dysfunction. Such disorders include stroke; cerebral ischemia; dysfunctions resulting from brain and/or spinal trauma; hypoxia and anoxia, such as from drowning, and including perinatal and neonatal hypoxic asphyxial brain damage; multi-infarct dementia; AIDS dementia; neurodegenerative diseases such as Alzheimer's disease, Parkinson's disease, Huntington's chorea, epilepsy, multiple sclerosis and amytrophic lateral sclerosis; brain dysfunction in connection with surgery involving extracorporeal circulation or in connection with brain surgery, including endarterectomy of the carotid arteries; and CNS dysfunctions as a result of exposure to neurotoxins or radiation. This utility is manifested, for example, by the ability of these compounds to inhibit delayed neuronal death in the gerbil bilateral occlusion model of ischaemia.

Anticonvulsant agents are useful in the clinic for the treatment of different types of convulsive states, such as, for example, epilepsy, status epilepticus, pre-eclampsia and delirium tremens. This ability is manifested, for example, by the ability of these compounds to inhibit seizures induced by various agents such as NMDLA.

The present invention relates to a compound having the general formula (1)

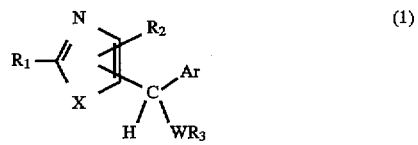

wherein:

X is O, S or Se;

$R_1$ is H, lower alkyl, lower alkoxy-lower alkyl, aryl-lower alkyl or $CF_3$ $R_2$ is H, lower alkyl, lower alkoxy-lower alkyl, aryl-lower alkyl or $CF_3$ W is O, S, NH or N-lower alkyl;

$R_3$ is H, lower alkyl or lower acyl;

Ar is phenyl, furyl, thienyl, naphthyl, pyridyl or pyrrolyl, optionally substituted by $R_6$;

$R_6$ is one or more groups selected from lower alkyl, lower acyl, halogen, lower alkoxy, $CF_3$, OH, $NO_2$ or $NR_4R_5$, wherein $R_4$ and $R_5$ independently are H, lower alkyl or lower acyl;

geometrical and optical isomers and racemates thereof where such isomers exist, as well as pharmaceutically acceptable acid addition salts thereof and solvates thereof;

and with the proviso that the following five compounds are excluded:

1-(4-methyl-5-thiazolyl)-1-phenylmethanol;

1-(2,4-dimethyl-5-oxazolyl)-1-phenylmethanol;

1-(5-thiazolyl)-1-phenylmethanol;

1-(4-oxazolyl)-1-phenylmethanol;

1-(2,4-dimethyl-5-thiazolyl)-1-(2-chlorophenyl) methanol.

The expression "pharmaceutically acceptable acid addition salts" is intended to include but is not limited to such salts as the hydrochloride, hydrobromide, hydroiodide, nitrate, hydrogen sulphate, dihydrogen phosphate, ethanedisulphonate, mesylate, fumarate, maleate and succinate.

Preferred embodiments of this invention relate to compounds having the general formula (2)

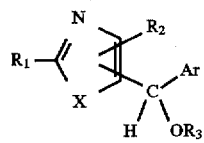 (2)

wherein:

X is O or S; and $R_1$, $R_2$, $R_3$ and Ar are as previously defined above.

Analogous compounds wherein X is Se, for example, 1-(3-furyl)-1-(4-methyl-5-selenazolyl)methanol and 1-(2-fluorophenyl)-1-(4-methyl-5-selenazolyl)methanol, are specifically included within the scope of the invention.

Throughout the specification and the appended claims, a given chemical formula or name shall encompass all geometrical and optical isomers and racemates thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term "lower alkyl" denotes a straight or branched alkyl group having from 1 to 6 carbon atoms. Examples of said lower alkyl include methyl, ethyl, n-propyl, isopropyl, n-butyl, isobutyl, t-butyl and straight- and branched-chain pentyl and hexyl.

Unless otherwise stated or indicated, the term "lower acyl" denotes a straight or branched acyl group having from 1 to 6 carbon atoms. Examples of said lower acyl include formyl, acetyl, propionyl, iso-butyryl, valeryl, and pivaloyl.

Unless otherwise stated or indicated, the term "lower alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight-and branched-chain pentoxy and hexoxy.

Unless otherwise stated or indicated, the term "halogen" shall mean fluorine, chlorine, bromine or iodine.

Unless otherwise stated or indicated, the term "lower alkoxy-lower alkyl" denotes a lower alkyl group as defined above substituted by a lower alkoxy group as defined above. Examples of said lower alkoxy-lower alkyl include methoxymethyl, ethoxymethyl, methoxyethyl and ethoxyethyl.

Unless otherwise stated or indicated, the term "aryl-lower alkyl" denotes a lower alkyl group as defined above substituted by a phenyl, naphthyl, furyl, thienyl, pyrrolyl or pyridyl group, itself optionally further substituted. Examples of said aryl-lower alkyl include benzyl, phenethyl, phenylpropyl, 4-fluorophenylmethyl, furfuryl, 3-furylmethyl, tolylethyl and thenyl.

Among the most preferred compounds of formula (1) according to the present invention are:

1-(3-furyl)-1-(4-methyl-5-thiazolyl)methanol;
1-(2-furyl)-1-(4-methyl-5-thiazolyl)methanol;
1-(4-methyl-5-thiazolyl)-1-(2-thienyl)methanol;
1-(4-methyl-5-thiazolyl)-1-(3-thienyl)methanol;
1-(2-fluorophenyl)-1-(4-methyl-5-thiazolyl)methanol;
1-(3-chlorophenyl)-1-(4-methyl-5-thiazolyl)methanol;
1-(4-methyl-5-oxazolyl)-1-phenylmethanol;
1-(4-fluorophenyl)-1-(4-methyl-5-oxazolyl)methanol;
1-(2-fluorophenyl)-1-(4-methyl-5-oxazolyl)methanol;
1-(3-aminophenyl)-1-(4-methyl-5-thiazolyl)methanol;
1-(3-dimethylaminophenyl)-1-(4-methyl-5-thiazolyl)-methanol;

and pharmaceutically acceptable acid addition salts or solvates thereof.

The present invention also relates to processes for preparing the compound having formula (1). Throughout the following general description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups are described, for example, in "Protective Groups in Organic Synthesis", T. W. Greene, Wiley-Interscience, New York, 1981.

Said compound wherein W is O may be prepared by (a) reacting a compound of general formula (3) with an organometallic derivative ArM

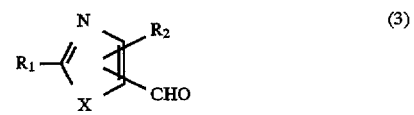 (3)

or (b) reacting a compound of general formula (4) with an organometallic derivative of general formula (5)

 (4)

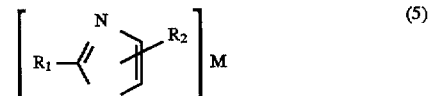 (5)

or (c) by reduction of a compound of general formula (6)

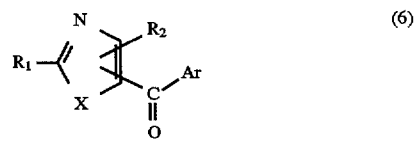 (6)

and quenching the reaction mixture with a proton source ($R_3$ is H) or an alkylating ($R_3$ is lower alkyl) or acylating ($R_3$ is lower acyl) reagent. Alternatively, the compound of formula (1) wherein W is O and $R_3$ is H may be first obtained as above and then converted into the compound wherein $R_3$ is lower alkyl or lower acyl.

The processes (a) or (b) can be achieved for example, by reacting together an aldehyde of structure (3) or (4) with a preformed organometallic derivative ArM or (5) respectively in a suitable anhydrous solvent such as diethylether, tetrahydrofuran or hexane or mixtures thereof. Said reaction should be conducted at a suitable temperature, normally between −100° C. and +50° C. and preferably under an inert atmosphere, normally nitrogen or argon. In a specific variation, a solution of the aldehyde of structure (3) or (4) in anhydrous diethylether or tetrahydrofuran is added dropwise to the organometallic derivative ArM or (5) respectively in anhydrous diethylether or tetrahydrofuran or hexane or mixtures thereof at a temperature of about −50° C. to −78° C. and under an atmosphere of nitrogen. After a suitable period of time the reaction mixture is allowed to warm to room temperature and then quenched by the addition of water or a lower alcohol. The required product (1) wherein $WR_3$ is OH may then be isolated and purified and characterised using standard techniques.

Aldehydes of general formula (3) or (4) and ketones of general formula (6) are either compounds which are commercially available or have been previously described in the literature, or compounds which can be prepared by the straightforward application of known methods.

Thus, the present invention also refers to some new intermediates of the general formula (6), namely:

a compound of general formula (6)

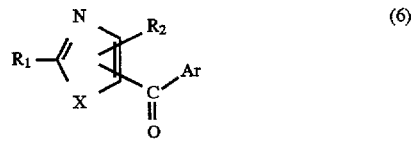

wherein $R_1$, $R_2$, X and Ar are as defined above with the provisos that when Ar represents phenyl, then $R_1$, $R_2$ and $R_6$ are not all hydrogen; and that the following three compounds are excluded:

4-bromophenyl 5-thiazolyl ketone;

4-methyl -5-thiazolyl phenyl ketone;

4-methoxyphenyl 4-methyl -5-thiazolyl ketone.

In the organometallic derivatives of general formula ArM or (5), M represents a metallic residue such as Li or Mg-halogen. Such compounds are either commercially available or have been previously described in the literature, or can be prepared by the straightforward application of known methods of organometallic chemistry.

Compounds of formula (1) wherein W is NH or N-lower alkyl may be prepared, for example, (a) by reductive amination of a ketone of general formula (6), or (b) by conversion of a ketone of general formula (6) to an oxime derivative followed by reduction, or (c) by conversion of a compound of general formula (1) wherein $WR_3$ is OH into the corresponding azide or phthalimide using, for example, the Mitsunobu reaction, and then reduction or hydrolysis respectively.

Compounds of general formula (1) contain an asymmetric centre and can thus exist in enantiomeric forms. These enantiomers may be separated using methods that will be well known to one skilled in the art. Such methods include, for example, (i) direct separation by means of chiral chromatography, for example, by HPLC using a chiral columns;

or (ii) recrystallisation of the diastereomeric salts formed by reacting the base (1) with an optically active acid;

or (iii) derivatization of the compound of formula (1) by reaction with an optically active reagent, separation of the resultant diastereoisomeric derivatives by, for example, crystallisation or chromatography, followed by regeneration of the compound of formula (1).

Alternatively, compounds of formula (1) may be obtained directly in an optically active form by using a chemical or enzymatic based method of asymmetric synthesis.

Pharmacology

The neuroprotective properties of the compounds of formula (1) are exemplified by their ability to inhibit delayed neuronal death in the gerbil bilateral occlusion model of ischaemia.

Animals used were male Mongolian gerbils (60–80g). Drugs were dissolved in isotonic saline containing dimethylsulphoxide.

Ischaemia was induced in the gerbils by 5 minute occlusion of both carotid arteries following the procedure described by R. Gill, A. C. Foster and G. N. Woodruff, J. Neuroscience. 1987, 7, 3343–3349. Body temperature was maintained at 37° C. throughout. Restoration of blood flow after occlusion was checked visually and the animals were allowed to survive for 4 days. The extent of neuronal degeneration in the hippocampus was then assessed. The test compounds were administered (i.p.) as a single dose 60 minutes following occlusion. No administration was made prior to the occlusion. The effectiveness of the compounds of formula (1) in decreasing damage to the CA1/CA2 hippocampal neurones in gerbils following ischaemic insult clearly illustrates the usefulness of these compounds in preventing neurodegeneration. These compounds are therefore expected to be of value in the treatment of acute and chronic neuropsychiatric disorders characterised by progressive processes that sooner or later lead to neuronal cell death and dysfunction.

The anticonvulsant properties of the compounds of formula (1) are exemplified by their ability to protect mice from NMDLA induced seizures. Male TO mice (18–30g) were used.

Groups of eight mice were injected with NMDLA (300 mg/kg i.p.) and the number of mice demonstrating tonic convulsions within the following 15 min period were recorded. Drugs were administered 15 min before the NMDLA, and data are expressed as the dose required to decrease the incidence of tonic convulsions by 50% ($ED_{50}$).

The sedative properties of the compounds of formula (1) are exemplified by their ability to inhibit the locomotor activity of mice.

The test drug was administered to mice and starting 20 min later locomotor activity was recorded for a 10 min period. Activity was monitored using an infra-red light beam interruption system in cages measuring 40cm×40cm. Data are expressed as the dose required to reduce locomotor activity by 50% ($ED_{50}$).

Pharmaceutical Formulations

The administration in the novel method of treatment of this invention may conveniently be oral, rectal, topical or parenteral at a dosage level of, for example, about 0.01 to 1000 mg/kg, preferably about 1.0 to 500 mg/kg and especially about 5.0 to 200 mg/kg and may be administered on a regimen of 1 to 4 doses or treatments per day. The dose will depend on the route of administration, preferred routes being oral or intravenous administration. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral solutions or suspensions for parenteral administration; or as suppositories for rectal administration; or as suitable topical formulations. Conventional procedures for the selection and preparation of suitable pharmaceutical formulations are described, for example, in "Pharmaceuticals—The Science of Dosage FormDesign", M. E. Aulton, Churchill Livingstone, 1988.

To produce pharmaceutical formulations containing a compound according to the present invention in the form of dosage units for oral application the active substance may be admixed with an adjuvant/a carrier e.g. lactose, saccharose, sorbitol, mannitol, starches such as potato starch, corn starch or amylopectin, cellulose derivatives, a binder such as gelatine or polyvinyl-pyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.02% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man skilled in the art.

Solutions for parenteral applications by injection can be prepared in an aqueous solution of a water-soluble pharmaceutically acceptable salt of the active substance, preferably in a concentration of from about 0.54% to about 10% by weight. These solutions may also contain stabilizing agents and/or buffering agents and may involve the use of surface acting agents to improve solubility. They may conveniently be provided in various dosage unit ampoules.

The necessary starting materials for all Examples were purchased commercially except as follows:

4-methy-5-thiazolecarbaldehyde (J. Amer. Chem. Soc., 1982, 104, 4934–43);
2-furyllithium (J. Org. Chem., 1962, 27, 1216).

Example 1

1-(3-Furyl)-1-(4-methyl-5-thiazolyl)methanol

4-Methylthiazole (3g) in dry diethyl ether was added dropwise to a stirred solution of n-butyllithium (1.6M in hexanes, 21ml) in diethyl ether (20ml) at −78° C. under an atmosphere of dry nitrogen. After 30 minutes, trimethylsilylchloride (3.9ml) was added and the mixture was then allowed to warm to 0° C. The mixture was then cooled to −78° C. and further n-butyllithium (21ml) was added. The mixture was warmed to 0° C. After 30 minutes the mixture was again cooled to −78° C. and 3-furaldehyde (5g) in diethyl ether (10ml) was added. The mixture was allowed to warm to room temperature and after 30 minutes saturated aqueous sodium hydrogen carbonate was added. The reaction mixture was extracted with diethyl ether in the usual manner to give the crude product which was then purified by flash chromatography on silica gel to give the title compound. M.p. 44°–46° C.

$^{13}$C Nmr (CDCl$_3$) 14.8, 62.4, 108.8, 128.3, 135.7, 139.4, 143.5, 148.1 and 150.9 ppm.

Found: C, 55.0; H, 4.7; N, 7.0. C$_9$H$_9$NO$_2$S requires C, 55.4; H, 4.6; N, 7.24%

Following the general method of Example I and using the appropriate aldehyde, the compounds of Examples 2 to 23 were prepared.

Example 2

1-(4-Methyl-5-thiazolyl)-1-(4-pyridyl)methanol

M.p. 131°–132° C.

Example 3

1-(4-Methyl-5-thiazolyl)-1-(3-pyridyl)methanol

The title compound was converted into the hydrochloride salt using hydrogen chloride in ethanol and diethyl ether. M.p. 180°–184° C. (dec.).

Example 4

1-(4-Methyl-5-thiazolyl)-1-(2-naphthyl)methanol

The title compound was characterised as the hydrochloride salt. M.p. 176°–180° C. (dec.).

Example 5

1-(2-Furyl)-1-(4-methyl-5-thiazolyl)methanol

M.p. 50°–51° C.

$^1$H Nmr (CDCl$_3$) 2.35 (3H, s), 6.08 (1H, s), 6.19 (1H, dt), 6.33 (1H, dq), 7.39 (1H, q) and 8.6 (1H, s) ppm.

Found: C, 55.1; H, 4.8; N, 6.8. C$_9$H$_9$NO$_2$S requires C, 55.4; H, 4.6; N, 7.2%

Example 6

1-(4-Methyl-5-thiazolyl)-1-(2-thienyl) methanol

M.p. 75°–77° C.

$^1$H Nmr (CDCl$_3$) 2.4 (3H, s), 3.46 (1H, d), 6.34 (1H, d), 6.95 (2H, m), 7.29 (1H, m) and 8.6 (1H, s) ppm.

Example 7

1-(4-Methyl-5-thiazolyl)1-(5-nitro-2-furyl)methanol
M.p. 127°–129° C.

Example 8

1-(5-Methyl-2-2-furyl)-1-(4-methyl-5-thiazolyl) methanol

M.p. 123°125° C.

Example 9

1-(1-Methyl-2-pyrrolyl)-1-(4-methyl-5-thiazolyl) methanol

M.p. 142°147° C. (dec.).

Example 10

1-(4-Methyl-5-thiazolyl)-1-(3thienyl)methanol $^1$H Nmr (CDCl$_3$) 2.43 (3H, s), 6.2 (1H, s), 7.06, 7.27 and 7.34 (each 1H, m) and 8.62 (1H, s) ppm.

Example 11

1(2-Fluorophenyl)-1-(4-methyl-5-thiazolyl)methanol

M.p. 100°101° C.

$^1$H Nmr (CDCl$_3$) δ2.45 (3H, s), 2.8 (1H, d), 6.42 (1H, d), 7.04, 7.19, 7.30 and 7.56 (each 1H, m) and 8.62 (1H, s) ppm.

Found: C, 58.95; H, 4.6; N, 6.0. C$_{11}$H$_{10}$FNOS requires C, 59.2; H, 4.55 N, 6.3%

Example 12

1-(3-Fluorophenyl)-1-(4-methyl-5-thiazolyl) methanol

M.p. 74°–75.5° C.

Found: C, 59.2; H, 4.4; N, 6.0. C$_{11}$H$_{10}$FNOS requires C, 59.2; H, 4.5; N, 6.3%

Example 13

1-4-Fluorophenyl)-1-(4-methyl-5-thiazolyl)methanol

M.p. 98.5°–100° C.

Example 14

1-(3-Chlorophenyl)-1-(4-methyl-5-thiazolyl) methanol

M.p. 97°–98° C.

$^1$Nmr (CDCl$_3$) 2.41 (3H, s), 3.37 (1H, d), 6.07 (1H, d), 7.26 (3H, m), 7.41 (1H, m) and 8.59 (1H, s) ppm.

Found: C, 55.2; H, 4.25; N, 5.65. C$_{11}$H$_{10}$ClNOS requires C, 55.1; H, 4.2; N, 5.8%

Example 15

1-(3-Methoxyphenyl)-1-(4-methyl-5-thiazolyl) methanol

M.p. 87°–88° C.

Found: C, 60.0; H, 5.7; N, 5.75. C$_{12}$H$_{13}$NO$_2$S. 0.25 H$_2$O requires C, 60.1; H, 5.7; N, 5.8%

Example 16

1-(2-Methoxyphenyl)-1-(4-methyl-5-thiazolyl) methanol M.p. 121°–122° C.

Example 17

1-(2-Chlorophenyl)-1-(4-methyl-5-thiazolyl) methanol

M.p. 122°–123° C.

Found: C, 55.05; H, 4.3; N, 5.8. C$_{11}$H$_{10}$ClNOS requires C, 55.1; H, 4.2; N, 5.8%

Example 18

1-(2-Methylphenyl)-1-(4-methyl-5-thiazolyl) methanol

M.p. 141.5°–143° C.

Found: C, 65.7; H, 6.2; N, 6.25. C$_{12}$H$_{13}$NOS requires C, 65.7; H, 6.0; N, 6.4%

Example 19

1-(3-Methenylphenyl)-1-(4-methyl-5-thiazolyl) methanol

M.p. 103°–104.5° C.

Found: C, 65.8; H, 6.25; N, 6.4. C$_{12}$H$_{13}$NOS requires C, 65.7; H, 6.0; N, 6.4%

Example 20

1-(4-Methyl-5-thiazolyl)-1-(3-nitrophenyl)methanol

M.p. 119.5°–121° C.

Example 21

1-(2,6-Dimethoxphenyl)-1-(4-methyl-5-thiazolyl) methanol

M.p. 125°–126° C.

Example 22

1-(4-Methyl-5-thiazolyl)-1-(1-naphthyl)methanol

M.p. 115.5°–116.5° C.

Example 23

1-(4-Methyl-5-thiazolyl)-1-3-trifluoromethylphenyl)methanol

M.p. 73.5°–75° C.

Found: C, 52.6; H, 3.5; N, 5.0. C$_{12}$H$_{10}$F$_3$NOS requires C, 52.7; H, 3.7; N, 5.1%

Example 24

1-(4-Chlorophenyl)-1-(4-methyl-5-thiazolyl) methanol

4-Methylthiazole was treated sequentially with n-butyllithium, trimethylsilylchloride, n-butyllithium and trimethylsilylchloride according to the method of J. Org. Chem., 1988, 53, 1748–61. Column chromatography on silica gel then gave 4-methyl-5-trimethylsilylthiazole.

4-Methyl-5-trimethylsilylthiazole (3 g), 4-chlorobenzaldehyde (4.9 g) and caesium fluoride (2.7 g) in dry tetrahydrofuran (150 ml) were heated under reflux for 30 hours. The mixture was cooled, evaporated to dryness and the residue thus obtained was purified by flash chromatography to afford the title compound. M.p. 133.5°–134.5° C.

Hydrochloride, m.p. 167.5°–172.5° C.

Following the general method of Example 24 and using the appropriate aldehyde, the compounds of Examples 25 and 26 were prepared.

Example 25

1-(2,4-Dichlorophenyl)-1-(4-methyl-5-thiazolyl) methanol

M.p. 163°–164° C.

Example 26

1-(3,4-Dichlorophenyl)-1-(4-methyl-5-thiazolyl) methanol

M.p. 143°–144° C.

Hydrochloride, m.p. 180°–188° C. (dec.).

Methanesulphonate, m.p. 147°–148° C.

Example 27

1-(3,4-dichlorophenyl)-1-(5-thiazolyl)methanol

2-Bromothiazole (5 g) in dry diethyl ether (20 ml) was added dropwise to a stirred solution of n-butyllithium (1.6M in hexanes, 21 ml) in diethyl ether (20 ml) at −70° C. under an atmosphere of dry nitrogen. After 30 minutes, trimethylsilylchloride (3.9 ml) was added and the mixture was allowed to warm to 0° C. The mixture was then cooled to −70° C. and further n-butyllithium (21 ml) was added. The mixture was warmed to 0° C. and after 30 minutes was cooled again to −70° C. and 3,4-dichlorobenzaldehyde (5.8 g) in diethyl ether (40 ml) was added. The mixture was then allowed to warm to room temperature and after 30 minutes saturated aqueous sodium hydrogen carbonate was added. The mixture was extracted with dichloromethane and the material thus obtained was purified by chromatography on silica gel to give the title compound. The hydrochloride salt was prepared. M.p. 167°–170° C.

Example 28

1-(4-Methyl-5-oxazolyl)-1-phenylmethanol

4-Methyl-5-oxazolecarbaldehyde (600 m g) in dry tetrahydrofuran (10 ml) was added dropwise to a stirred solution of phenyllithium (2.0M solution in cyclohexane and diethyl ether, 2.8 ml) in tetrahydrofuran (20 ml) at −70° C. under an atmosphere of dry nitrogen. After 1 hour the mixture was allowed to warm to room temperature. After a further 1 hour saturated aqueous sodium hydrogen carbonate was added and the mixture was extracted with ethyl acetate. The product was purified by flash chromatography to yield the title compound.

M.p. 79°–81° C.

$^1$H Nmr (CDCl$_3$) 2.14 (3H, s), 5.94 (1H, s), 7.3–7.5 (5H, m) and 7.75 (1H, s) ppm.

Example 29

1-(4-Fluorophenyl)-1-4-methyl-5-oxazolyl)methanol

4-Methyl-5-oxazolecarbaldehyde (770 mg) in dry tetrahydrofuran (15 ml) was added dropwise to a stirred solution of 4-fluorophenyl magnesium bromide (1M solution in tetrahydrofuran, 7.3 ml) in tetrahydrofuran (30 ml) at −70° C. under an atmosphere of dry nitrogen. After 1 hour the mixture was allowed to warm to room temperature and was then poured into saturated aqueous sodium hydrogen carbonate. Extraction with ethyl acetate followed by flash chromatography gave the title compound.

M.p. 102.5°–104° C.

$^1$H Nmr (CDCl$_3$) 2.09 (3H, s), 3.68 (1H, br), 5.88 (1H, s), 7.04 (2H, m), 7.38 (2H, m) and 7.66 (1H, s) ppm.

Following the general method of Example 29 and using the appropriate Grignard reagent, the compounds of Examples 30 and 31 were prepared.

Example 30

1-(4-Methyl-5-oxazolyl)-1-(2-methylphenyl) methanol

M.p. 122°–123° C.

Example 31

1-(4-Methyl-5-oxazolyl)-1-(4-methylphenyl) methanol

M.p. 125°–127° C.

Example 32

1-(4-Methyl-5-oxazolyl)-1-(3-methylphenyl) methanol n-Butyllithium (2.5 solution in hexanes, 3.9 ml) was added dropwise to a stirred solution of 3-bromotoluene (1.1 ml) in dry tetrahydrofuran (20 ml) at −70° C. under an atmosphere of dry nitrogen. After 20 minutes, 4-methyl-5-oxazolecarbaldehyde (1.15 g) in tetrahydrofuran (10 ml) was added. After 1 hour the mixture was allowed to warm to room temperature and was then heated under reflux for 1 hour. The cooled solution was poured into saturated aqueous sodium hydrogen carbonate. Extraction with ethyl acetate and flash chromatography then gave the title confound. M.p. 76.5°–77.5° C.

Following the general method of Example 32 and using the appropriate aryl bromide or iodide, the compounds of Examples 33 to 36 were prepared.

Example 33

1-(2-Fluorophenyl)-1-(4-methyl-5-oxazolyl) methanol $^1$H Nmr (CDCl$_3$) 2.14 (3H, s), 3.02 (1H, br s), 6.22 (1H, s), 6.98–7.37 (3H, m) and 7.67 (2H, m) ppm.

Example 34

1-(2,4-Difluorophenyl)-1-(4-methyl-5-oxazolyl) methanol

M.p. 116°–117.5° C.

Example 35

1-(4-Methyl-5-oxazolyl)1-(2-trifluoromethyl-phenyl) methanol

M.p. 105.5°–107.5° C.

Found: C, 56.2; H, 3.7; N, 5.4. $C_{12}H_{10}F_3NO_2$ requires C, 56.0; H, 3.9; N, 5.45%

Example 36

1-(2-Chlorophenyl)-1-(4-methyl-5-oxazolyl) methanol

M.p. 127°–128° C.

Example 37

Methyl-1-(4-Methyl-5-thiazolyl)-1-phenylmethyl Ether

Sodium hydride (80% dispersion in mineral oil, 80 mg) was added to a stirred solution of 1-(4-methyl-5-thiazolyl)-1-phenyl-methanol (500 mg) in dry N,N-dimethylformamide (10 ml) at 0° C. After 10 minutes, methyl iodide (0.15 ml) was added. The mixture was allowed to warm to room temperature and after a further 30 minutes the mixture was evaporated to dryness. The residue was purified by flash chromatography to give the title confound.

$^1$H Nmr (CDCl$_3$) 2.46 and 3.39 (each 3H, s), 5.52 (1H, s), 7.28–7.4 (5H, m) and 8.64 (1H, s) ppm.

Following the general method of Example 37 and using the appropriate starting materials, the compounds of Example 38 to 43 were prepared.

Example 38

Methyl 1-(3,4-Dichlorolphenyl)-1-(4-methyl-5-thiazolyl)methyl Ether

Hydrochloride, m.p. 170°–176° C. (dec.).

Example 39

Methyl 1-(2,4-Dichlorophenyl)-1-(4-methyl-5-thiazolyl)methyl Ether

M.p. 55°–56° C.

Example 40

Ethyl 1-(3-Furyl)-1-(4-methyl-5-thiazolyl)methyl Ether $^{13}$C Nmr (CDCl$_3$) 15.1, 15.3, 64.3, 69.6, 109.0, 126.4, 133.1, 139.9, 143.6, 149.5 and 151.3 ppm.

Example 41

1-(3-Furyl)-1-(4-methyl-5-thiazolyl)methyl Methyl Ether $^1$Nmr (CDCl$_3$) 2.45 and 3.36 (each 3H, s), 5.52 (1H, s), 6.34 (1H, m), 7.38 (2H, m) and 8.68 (1H, s) ppm.

Example 42

1-(2-Furyl)-1-(4-methyl-5-thiazolyl)methyl Methyl Ether $^1$H Nmr (CDCl$_3$) 2.44 and 3.39 (each 3H, s), 5.57 (1H, s), 6.27 and 6.32 (each 1H, m), 7.41 (1H, m) and 8.7 (1H, s) ppm.

Example 43

1-(2-Fluorophenyl)-1-(4-methyl-5-thiazolyl)methyl Methyl Ether $^1$H Nmr (CDCl$_3$) 2.48 and 3.39 (each 3H, s), 5.86 (1H, s), 6.98–7.35 (3H, m), 7.52 (1H, m) and 8.65 (1H, s) ppm.

Example 44

1-(4-Methyl-5-thiazolyl)-1-phenylmethyl Acetate

Acetyl chloride (0.6 ml) was added to a solution of 1-(4-methyl-5-thiazolyl)-1-phenylmethanol (800 mg) and pyridine (0.5 ml) in dichloromethane (30 ml) at 0° C. under an atmosphere of dry nitrogen. The mixture was allowed to warm room temperature and was then stirred overnight. Evaporation and purification of the residue by flash chromatography gave the title compound.

$^1$H Nmr (CDCl$_3$) 2.15 and 2.51 (each 3H, s), 7.16 (1H, s), 7.35 (5H, m) and 8.66 (1H, s) ppm.

Example 45

1-(2-Fluorophenyl)-1-(4-methyl-5-thiazolyl)methyl Acetate

Starting with 1-(2-fluorophenyl)-1-(4-methyl-5-thiazolyl)methanol and using the method of Example 44, the title compound was prepared.

M.p. 53°–56° C.

Example 46

1-(3-Aminophenyl)-1-(4-methyl-5-thiazolyl)methanol 1-(4-Methyl-5-thiazolyl)-1-(3-nitrophenyl)methanol (2 g) and 10% palladium on charcoal (200 mg) in ethanol (60 ml) were shaken overnight under an atmosphere of hydrogen. The mixture was filtered and the filtrate was evaporated to dryness. The residue was converted into the hydrochloride salt, recrystallised and then reconverted into the title compound.

M.p. 137°–138° C.

$^1$H Nmr (CDCl$_3$) 2.38 (3H, s), 2.44 (1H, d), 3.65 (2H, br), 5.95 (1H, d), 6.56 (1H, m), 6.7 (2H, m) 7.08 (1H, m) and 8.57 (1H, s) ppm.

Found: C, 59.9; H, 5.55; N, 12.4. C$_{11}$H$_{12}$N$_2$OS requires C, 60.0; H, 5.5; N, 12.7%

Example 47

1-(3-Dimethylaminophenyl)-1-(4-methyl-5-thiazolyl)methanol

The title compound was prepared from 4-methyl-5-thiazolecarbaldehyde and 3-bromo-N,N-dimethylaniline using the method of Example 32. M.p. 135°–138° C.

$^1$H Nmr (CDCl$_3$) 2.44 (3H, s), 2.75 (1H, s), 2.96 (6H, s), 6.04 (1H, s), 6.65–6.8 (3H, m), 7.23 (1H, t) and 8.60 (1H, s) ppm.

Example 48

1-(3-Hydroxyphenyl)-1-(4-methyl-5-thiazolyl)methanol 1-(3-Methoxyphenyl)-1-(4-methyl-5-thiazolyl)methanol (1 g) in dry dichloromethane (10 ml) was added dropwise to boron tribromide (1M solution in dichloromethane, 25 ml) at 0° C. The mixture was allowed to warm to room temperature and was stirred for 15 minutes. The mixture was poured onto ice (40 g) and 0.88 ammonia (10 ml). The precipitate was filtered off and purified by chromatography to give the title compound. M.p. 181°–184° C.

Example 49

1-(2-Furyl)-1-(4-methyl-5-oxazolyl)methanol

The title compound was prepared from 4-methyl-5-oxazolecarbaldehyde and 2-furyllithium using the method of Example 28. M.p. 52°–54° C.

$^1$H Nmr (CDCl$_3$) 2.16 (3H), 2.7 (1H, br), 5.92, 6.32, 6.40, 7.44 and 7.80 (each 1H).

Found: C, 60.0; H, 5.1; N, 7.9. C$_9$H$_9$NO$_3$ requires C, 60.3; H, 5.1; N, 7.8%

Example 50

Resolution of 1-(4-Methyl-5-thiazolyl)-1-phenylmethanol 1-(4-Methyl-5-thiazolyl)-1-phenylmethyl acetate suspended in pH 7.5 buffer at 37° C. was treated with pig liver esterase. The resulting product was subjected to flash chromatography to give, after crystallisation, 1-(4-methyl-5-thiazolyl)-1-phenylmethanol which was shown by chiral HPLC to be greater than 98% one enantiomer. The 1-(4-methyl-5-thiazolyl)-1-phenylmethyl acetate that was also obtained from the flash chromatographywas subjected to base hydrolysis and the product recrystallised to give the other enantiomer of the title compound.

Example 51

Resolution of 1-(2-Fluorophenyl)-1-(4-methyl-5-thiazolyl) methanol

The title compound was resolved by preparative HPLC on a Chiralcel OD column using 2-propanol in hexane as solvent. The enantiomers showed $[\alpha]_D^{20}$+61° and −60° respectively.

Example 52

4-Methyl-5-oxazolecarbaldehyde

4-Methyl-5-oxazolecarbonyl chloride (Indian J. Chem., Sect. B, 1985, 24B, 535–8) in dry tetrahydrofuran was treated at −78° C. with lithium tri-tert-butoxyaluminihydrode (1M solution in tetrahydrofuran). Work up in the usual fashion gave the title compound.

$^1$H Nmr (CDCl$_3$) 2.55 (3H, s), 8.03 (1H, s) and 9.92 (1H, s) ppm.

Example 53

1-Azido-1-(3-furyl)-1-(4-methyl-5-thiazolyl) methane

Borontrifluoride diethyletherate (8 mmoles) was added to a mixture of the product from Example 1 (8 mmoles) and trimethylsilylazide (8 mmoles) in dry benzene (4 ml). The mixture was stirred at room temperature for 4 days and then diluted with ethyl acetate (50 ml). After washing with aqueous sodium hydrogen carbonate solution and water, the organic phase was separated and dried. Evaporation gave the title compound as an oil.

$^{13}$C Nmr (CDCl$_3$) 15.1, 53.9, 108.8, 123.9, 129.9, 140.0, 143.9, 150.3 and 151.4 ppm.

Example 54

1-Azido-1-(4-methyl-5-thiazolyl)-1-phenylmethane

Starting with 1-(4-methyl-5-thiazolyl)-1-phenylmethanol and using the general method of Example 53, the title compound was obtained.

$^{13}$C Nmr (CDCl$_3$) 15.4, 61.4, 126.6, 128.5, 128.8, 131.0, 138.5, 150.1 and 151.6 ppm.

Example 55

1-(4-Methyl-5-thiazolyl)-1-(N-phthalimido)-1-phenylmethane Hydrochloride 1-(4-Methyl-5-thiazolyl)-1-phenylmethanol (30 mmoles), triphenylphosphine (40 moles), phthalimide (40 mmoles) and diethyl azodicarboxylate (40 mmoles) in dry tetrahydrofuran (15 ml) were stirred at room temperature for 3 days. The mixture was evaporated to dryness and the residue was purified by column chromatography on silica gel. The material thus obtained was converted into the hydrochloride salt using the standard procedure.

M.p. 194°–196° C.

$^{13}$C Nmr (CDCl$_3$) 12.6, 49.1, 124.1, 127.0, 129.2, 129.4, 131.2, 134.7, 135.0, 135.8, 144.8, 154.7 and 167.2 ppm.

Example 56

1-(4-Methyl-5-thiazolyl)-1-phenylmethylamine

The product from Example 55 (1.3 mmoles) and hydrazine hydrate (1.8 mmoles) were heated under reflux in ethanol (10 ml) for 2 hours. The precipitated phthalimide was filtered off and the filtrate was evaporated to dryness. The residue thus obtained was purified by flash chromatography to yield the title compound.

$^{13}$C Nmr (CDCl$_3$) 15.4, 53.1, 126.4, 127.5, 128.6, 137.8, 143.9, 147.6 and 150.2 ppm.

Example 57

N-(1-(4-Methyl-5-thiazolyl)-1-phenylmethyl) acetamide

Acetyl chloride was added to a solution of the product from Example 56 and triethylamine in dry dichloromethane. The mixture was stirred at room temperature overnight and then washed with aqueous sodium hydrogen carbonate solution. The organic phase was separated, dried and evaporated and the residue was purified by flash chromatography to give the title compound.

$^{13}$C Nmr (CDCl$_3$) 15.3, 22.9, 50.1, 126.7, 128.0, 128.8, 133.5, 140.4, 150.0, 150.2 and 169.0 ppm.

Example 58

1-(3-Furyl)-1-(4-methyl-5-thiazolyl)methylamine

The product from Example 53 in ethanol was shaken with 10% palladium-on-charcoal under an atmosphere of hydrogen for 3 hours. The catalyst was filtered off and the filtrate was evaporated to dryness. Flash chromatography of the residue thus obtained gave the title compound.

$^{13}$C Nmr (CDCl$_3$) 14.7, 44.9, 108.6, 128.9, 137.0, 138.4, 142.9, 147.2 and 149.7 ppm.

Pharmacy Examples

The following examples illustrate suitable pharmaceutical compositions to be used in the method of the invention.

| Composition 1 - Tablets | |
|---|---|
| Compound of Example 33 | 10 g |
| Lactose | 94 g |
| Microcrystalline cellulose | 86 g |
| Polyvinylpyrrolidone | 8 g |
| Magnesium stearate | 2 g |

The compound of Example 33, lactose, cellulose and polyvinylpyrrolidone are sieved and blended. The magnesium stearate is sieved and then blended into the above mixture. Compression using suitable punches then yields 1000 tablets each containing 10mg of the active ingredient. If desired, the obtained tablets can then be film coated.

| Composition 2 - Tablets | |
|---|---|
| Compound of Example 11 | 50 g |
| Lactose | 80 g |
| Microcrystalline cellulose | 20 g |
| Potato starch | 40 g |
| Polyvinylpyrrolidone | 8 g |
| Magnesium stearate | 2 g |

The compound of Example 11, lactose, cellulose and part of the starch are mixed and granulated with 10% starch paste. The resulting mixture is dried and blended with the remaining starch, the polyvinylpyrrolidone and the sieved magnesium stearate. The resulting blend is then compressed to give 1000 tablets each containing 50 mg of the active ingredient.

| Composition 3 - Capsules | |
|---|---|
| Compound of Example 1 | 100 g |
| Pregelatinised starch | 98 g |
| Magnesium stearate | 2 g |

The compound of Example 1 and the starch are sieved, blended together and then lubricated with the sieved magnesium stearate. The blend is used to fill 1000 hard gelatine capsules of a suitable size. Each capsule contains 100 mg of the active ingredient.

| Composition 4 - Injection Formulation | |
|---|---|
| Compound of Example 46 | 0.5 to 10 g |
| Polyethoxylated castor oil | 15 g |
| Water for injection ad | 100 g |

Sodium chloride may be added to adjust the tonicity of the solution and the pH may be adjusted to that of maximum stability and/or facilitate solution of the compound of the invention using dilute acid or alkali or by the addition of suitable buffer salts. Antioxidants and metal chelating salts may also be included.

The solution is prepared, clarified and filled into appropriate size bottles and sealed. The formulation is sterilised by heating in an autoclave. Alternatively, the solution may be sterilised by filtration and filled into sterile bottles under aseptic conditions. The solution may be packed under a nitrogen blanket.

| Composition 5 - Injection Formulation | |
|---|---|
| Compound of Example 1 | 0.5 to 10 g |
| Polyethoxylated castor oil | 15 g |
| Propylene glycol | 20 g |
| Polyoxyethylene-polyoxypropylene block copolymer (Pluronic F68) | 10 g |
| Water for injection ad | 100 g |

The compound of the invention is added to a mixture of polyethoxylated castor oil, propylene glycol and Pluronic F68. The mixture is gently heated until a clear solution is obtained. This solution is sterilised by heating in an autoclave or alternatively, by the process of filtration. A concentrated sterile solution is thus obtained, which is suitable for dilution with sterile water in order to form a composition suitable for parenteral administration.

| Composition 6 - Injection Formulation | |
|---|---|
| Compound of Example 5 | 0.5 to 10 g |
| Hydroxypropyl-β-cyclodextrin | 10 g |
| Water for injection ad | 100 g |

Water for injection is added to a mixture of the compound of the invention and hydroxypropyl-β-cyclodextrin. The mixture is gently stirred until a clear solution is obtained. The solution is filled into bottles which are then sealed and sterilised by heating in an autoclave or alternatively, by the process of filtration.

We claim:

1. A compound having the formula (1)

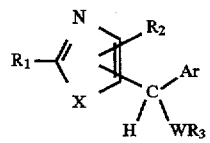
(1)

or a pharmaceutically acceptable acid salt or solvate thereof, in the form of an optical isomer or a racemate, wherein X is O, S or Se;

$R_1$ is H, lower alkyl, lower alkoxy-lower alkyl, aryl-lower alkyl or $CF_3$;

$R_2$ is H, lower alkyl, lower alkoxy-lower alkyl, aryl-lower alkyl or $CF_3$;

W is O, S, NH or N-lower alkyl;

$R_3$ is H, lower alkyl or lower acyl;

Ar is phenyl, furyl, thienyl, naphthyl, pyridyl or pyrrolyl, optionally substituted by $R_6$;

$R_6$ is one or more groups selected from lower alkyl, lower acyl, halogen, lower alkoxy, $CF_3$, OH, $NO_2$ or $NR_4R_5$, wherein $R_4$ and $R_5$ independently are H, lower alkyl or lower acyl; and with the proviso that the following five compounds are excluded:

1-(4-methyl-5-thiazolyl)-1-phenylmethanol;
1-(2,4-dimethyl-5-oxazolyl)-1-phenylmethanol;
1-(5-thiazolyl)-1-1-phenylmethanol;
1-(4-oxazolyl)-1-phenylmethanol;
1-(2,4-dimethyl-5-thiazolyl)-1-(2-chlorophenyl) methanol.

2. A compound according to claim 1 having the formula (2)

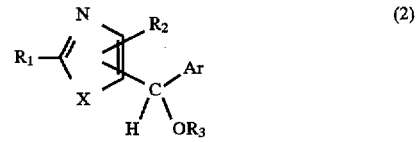
(2)

wherein:

X is O or S.

3. A compound according to claim 1 which is:

1-(3-furyl)-1-(4-methyl-5-thiazolyl)methanol;
1-(2-furyl)-1-(4-methyl-5-thiazolyl)methanol;
1-(4-methyl-5-thiazolyl)-1-(2-thienyl)methanol;
1-(4-methyl-5-thiazolyl)-1-(3-thienyl)methanol;
1-(2-fluorophenyl)-1-(4-methyl-5-thiazolyl)methanol;
1-(3-chlorophenyl)-1-(4-methyl-5-thiazolyl)methanol;
1-(4-methyl-5-oxazolyl)-1-phenylmethanol;
1-(4-fluorophenyl)-1-(4-methyl-5-oxazolyl)methanol;
1-(2-fluorophenyl)-1-(4-methyl-5-oxazolyl)methanol;
1-(3-aminophenyl)-1-(4-methyl-5-thiazolyl)methanol;
1-(3-dimethylaminophenyl)-1-(4-methyl-5-thiazolyl) methanol;

or a pharmaceutically acceptable acid addition salt or solvate thereof.

4. A pharmaceutical formulation containing a compound according to claim 1 having the general formula (1)

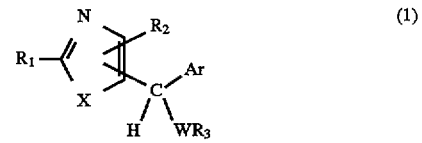
(1)

as active ingredient and a pharmaceutically acceptable carrier.

5. A method for the treatment of neurodegenerative disorders resulting from or associated with ischemia, which comprises administering to a host in need of such treatment a sufficient amount of a compound having the formula (1)

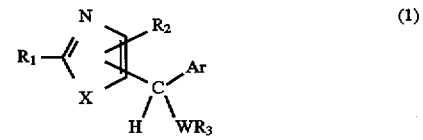
(1)

or a pharmaceutically acceptable acid salt or solvate thereof, in the form of an optical isomer or a racemate, wherein X is O, S or Se;

$R_1$ is H, lower alkyl, lower alkoxy-lower alkyl, aryl-lower alkyl or $CF_3$;

$R_2$ is H, lower alkyl, lower alkoxy-lower alkyl, aryl-lower alkyl or $CF_3$;

W is O, S, NH or N-lower alkyl;

$R_3$ is H, lower alkyl or lower acyl;

Ar is phenyl, furyl, thienyl, naphthyl, pyridyl or pyrrolyl, optionally substituted by $R_6$; and $R_6$ is one or more groups selected from lower alkyl, lower acyl, halogen, lower alkoxy, $CF_3$, OH, $NO_2$ or $NR_4R_5$, wherein $R_4$ and $R_5$ independently are H, lower alkyl or lower acyl.

6. The method according to claim 5, wherein the disorder is stroke; cerebral ischemia; multi-infarct dementia; or a dysfunction resulting from brain trauma, spinal trauma, hypoxia, anoxia, perinatal hypoxic asphyxial brain damage or neonatal hypoxic asphyxial brain damage.

* * * * *

UNITED STATES PATENT AND TRADEMARK OFFICE
CERTIFICATE OF CORRECTION

PATENT NO. : 5,712,299
DATED : Jan. 27, 1998
INVENTOR(S) : Boar et al.

It is certified that error appears in the above-indentified patent and that said Letters Patent is hereby corrected as shown below:

On the title page "[30] Foreign Application Priority Data," change "July 3, 1993" to --July 6, 1993--, and "9302324" to --9302334--; and col. 18, lines 46-52, delete "having the general formula(1)

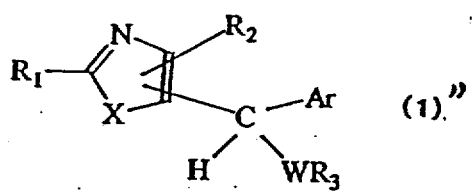

Signed and Sealed this

Twenty-eighth Day of July, 1998

Attest:

BRUCE LEHMAN

Attesting Officer                Commissioner of Patents and Trademarks